United States Patent [19]
Rohe et al.

[11] Patent Number: 5,567,944
[45] Date of Patent: Oct. 22, 1996

[54] COMPTON CAMERA FOR IN VIVO MEDICAL IMAGING OF RADIOPHARMACEUTICALS

[75] Inventors: Ronald C. Rohe, Hamilton; John D. Valentine, Cincinnati, both of Ohio

[73] Assignee: University of Cincinnati, Cincinnati, Ohio

[21] Appl. No.: 430,414

[22] Filed: Apr. 28, 1995

[51] Int. Cl.⁶ ........................................... G01T 1/24
[52] U.S. Cl. .................. 250/370.09; 250/370.1; 250/363.03
[58] Field of Search ................ 250/370.09, 370.1, 250/370.11, 370.08, 363.02, 363.1, 369

[56] References Cited

U.S. PATENT DOCUMENTS

| | | |
|---|---|---|
| 4,529,882 | 7/1985 | Lee . |
| 4,857,737 | 8/1989 | Kamae et al. . |
| 5,175,434 | 12/1992 | Engdahl . |

OTHER PUBLICATIONS

"Towards Direct Reconstruction from a Gamma Camera Based on Compton Scattering", IEEE Transactions on Medical Imaging, vol. 13, No. 2, Jun. 1994 by Michael J. Cree and Philip J. Bones.

"High Performance, Thermoelectrically Cooled X–Ray and Gamma Ray Detectors" by A. C. Huber, J. A. Pantazis, and V. T. Jordanov; Invited paper at the International Conference on the Application of Accelerators in Research and Industry, Denton, Texas, Nov. 1994.

Primary Examiner—David P. Porta
Assistant Examiner—Richard Hanig
Attorney, Agent, or Firm—Wood, Herron & Evans, P.L.L.

[57] ABSTRACT

A source emitting gamma rays of discrete energy is imaged using a Compton type scattering camera. The source location of emitted gamma rays is determined from primary and secondary interaction positions and the energy deposited ($\Delta E$) when the gamma-ray Compton scatters mainly from a primary detector system. $\Delta E$ is mainly determined by measuring the energy of the scattered gamma ray when it interacts in a secondary detector system and subtracting this value from a known energy value of the emitted gamma ray. Gamma rays that undergo only one Compton scatter interaction in the primary detector system are emphasized or preferred in the image reconstruction. The present invention optimizes the materials, geometries, and electronics of the primary and secondary detector system so as to maximize the occurrence and acquisition of these preferred events while simultaneously maintaining close proximity of primary system to the photon source as well as high energy resolution in the secondary detector system. By collecting interaction data from a large number of emitted gamma rays, the source image can be reconstructed.

17 Claims, 3 Drawing Sheets

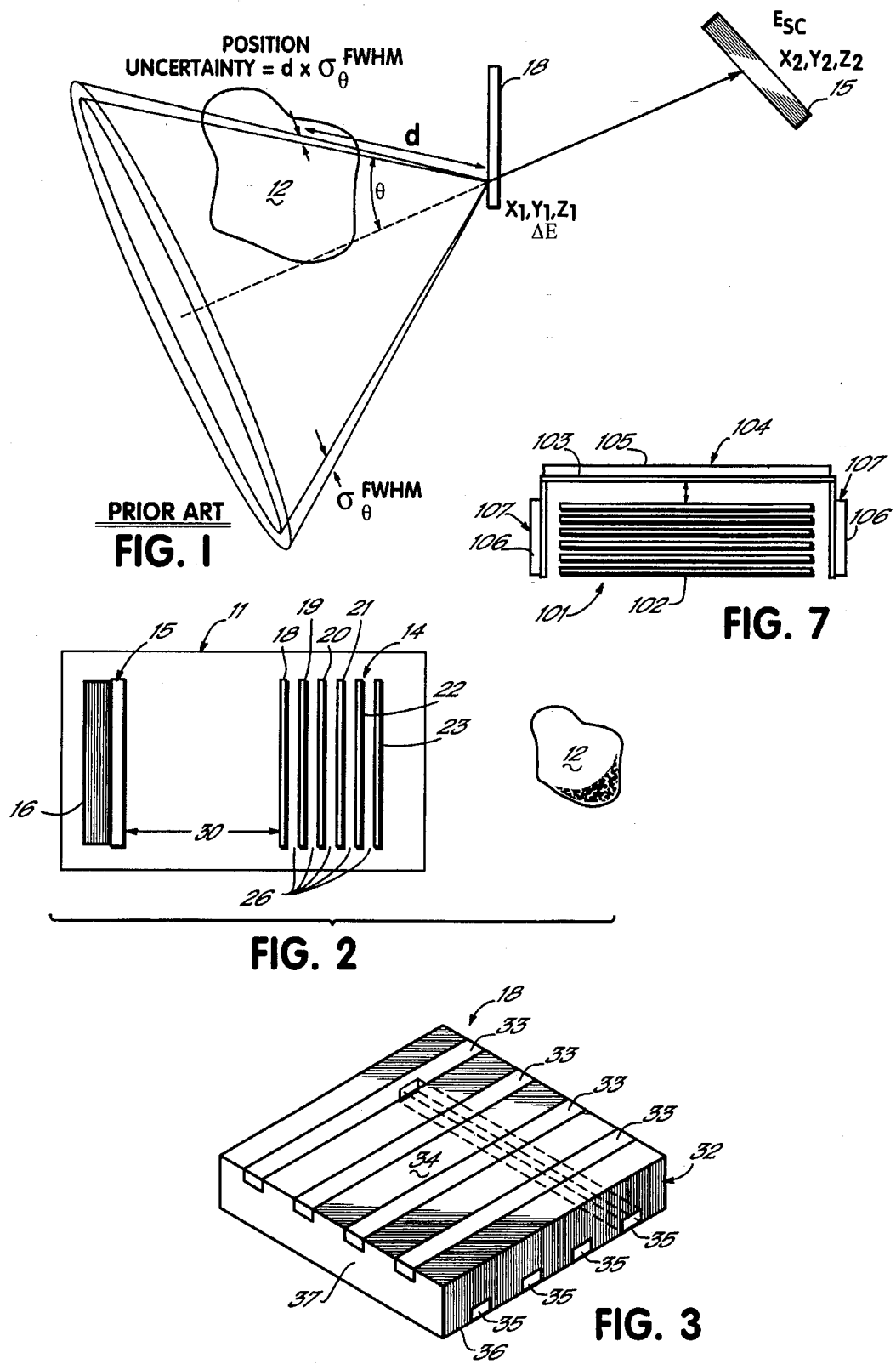

COMPTON CAMERA FOR IN VIVO MEDICAL IMAGING OF RADIOPHARMACEUTICALS

BACKGROUND OF THE INVENTION

Nuclear medicine imaging is an extremely important tool used in the diagnosis and treatment of numerous different ailments. This generally involves injection of a radiopharmaceutical such as a technetium-99m complex or a iodine-131 complex which localizes in one or more areas or organs of the body. These radiopharmaceuticals will then emit gamma rays which can be detected to provide an image of the organ and/or tissue.

The Anger camera is the most commonly used image-formation device in nuclear medicine. The Anger camera uses a scintillation crystal, such as sodium iodide crystal, which absorbs gamma rays to produce light. An array of photomultiplier tubes adjacent to the crystal detects the light and amplifies the signal so as to indicate the location of the gamma-ray interaction and produce a two-dimensional plane-projected image of the object.

Anger cameras use lead collimators in order to eliminate all gamma rays excepting those which have a particular angle-of-incidence upon the camera face. The collimator, in effect, filters out the vast majority of gamma rays emitted from a source. But the collimator is required in order to achieve any usable spatial resolution.

Typically, with a state-of-the-art, triple-headed Anger camera, only one in 1,000 to 1,500 of emitted gamma rays are detected by the camera. The remainder are filtered out by the collimators. This requires an increased number of gamma rays in order to obtain a usable image. In order to achieve this, one can increase the radiation dose and/or increase the time for which the Anger camera is exposed to the source. Neither of these are particularly desirable.

Another problem, of course, with the lead collimators is weight. In certain applications particularly, very large plates of lead are required which may require special handling equipment such as booms and extra floor supports, drastically increasing the overall cost and decreasing the convenience of use.

A second method of imaging gamma rays in Nuclear Medicine is a Compton scatter camera. It has been suggested over the years to use Compton scattering to provide an image of a radiation source. Such a device is disclosed by Cree et al. (Cree, Michael J. and Philip J. Bones, *Towards Direct Reconstruction from a Gamma Camera Based on Compton Scattering*, IEEE TRANSACTIONS ON MEDICAL IMAGING, Vol. 13, No. 2, June 1994, pp. 398–407). Basically, a Compton scatter camera consists of two detector systems, herein called the primary and secondary (although some designs, e.g., multiple scatter cameras, do not make this distinction). The primary detector system, closest to the source, is designed so that the Compton scattering—that is, the scattering interaction between the gamma ray and an electron—is measured while the secondary detector system absorbs the scattered gamma rays and measures their energy. The idea is that a gamma ray emitted from the source is reasonably likely to undergo Compton scattering in the primary detector system, wherein the position and energy of the interaction are measured, then be absorbed in the secondary detector system wherein the position and energy of absorption are measured. From this, the location of the gamma-ray source can be determined, (after acquisition and reconstruction of data for numerous emissions).

FIG. 1 shows a diagrammatic depiction of these two types of interaction. For simplicity, the detector systems are depicted as planar arrays in FIG. 1. The angle of Compton scatter $\theta$ in the primary detector system can be calculated from the energy deposited in the primary detector $\Delta E$ by $$\cos \theta = 1 - \frac{mc^2 \, \Delta E}{(E_0 - \Delta E) E_0}$$

where $E_o$ is the initial gamma-ray energy, m is the electron mass, and c is the speed of light. This provides sufficient data to restrict the location of the original gamma-ray emission to a cone surface whose apex is centered at the location of the primary detector Compton scatter interaction, and whose axis is determined by the locations of the primary and secondary system interactions. Enough of these cone profiles will give sufficient information to reconstruct the original emission source distribution.

To be included in the reconstruction of the original radioisotope distribution, the Compton scatter camera minimally requires four pieces of information for each emitted gamma ray: (1) initial energy of the emitted gamma ray ($E_o$); (2) location of the first Compton scatter interaction; (3) location of the second interaction (Compton scatter or photoelectric absorption); and (4) energy deposited by the first Compton scatter interaction ($\Delta E$). The following formula gives the resulting energy ($E_{sc}$) of a gamma ray after it has Compton scattered off a free electron.

$$E_{SC} = \frac{E_0}{[1 + \alpha(1 - \cos \theta)]} \qquad \alpha = \frac{E_o}{mc^2}$$

FIG. 1 shows the geometry involved in a typical good event in a Compton scatter camera. One of the significant problems of an effective Compton camera is determining $\Delta E$. As indicated by Cree et al., the energy resolution in the primary (first) detector limits the resolution of scattering angle, and this angular resolution is itself dependent on the scattering angle. In the past, this has been resolved by providing primary detectors that have high energy resolution. Such high energy resolution detectors often require liquid nitrogen cooled semiconductor arrays which are edge-mounted to the thermal sink for minimal interference with transmitted and scattered gamma rays.

An array of detectors is required in order to optimally provide x, y and z position of the initial Compton scattering interaction in the primary detector system. This requires a very large physical surface area. Further, cryogenically cooling the primary detector system, which will be closest to the radiation source (the patient's body), provides significant difficulties. This must also be accomplished while, at the same time, providing a secondary detector system in sufficiently close physical proximity to the primary detector system to efficiently intercept and detect the Compton scattered gamma rays—that is, the absorption of the Compton scattered gamma rays by the secondary detector system.

Basically, this assumed requirement of high energy resolution in the primary detector system has posed technical difficulties which have prevented the commercialization of Compton scatter cameras for use in medical imaging. Although these devices have been suggested for medical imaging as, for example, in U.S. Pat. Nos. 5,175,434, 4,857,737 and 4,529,882 and the references cited therein, to date there is no commercial Compton scattering camera available for medical use. The Anger camera remains the primary workhorse for this application.

SUMMARY OF THE INVENTION

The present invention is premised on the realization that the limitations of the Compton scattering camera can be eliminated by taking direct advantage of the discrete energy nature of the gamma-ray sources that are used in nuclear medicine. By optimizing the cameras design for emphasizing the acquisition of (and reconstruction by) those gamma rays which undergo a single Compton interaction in the primary detector system, followed by total absorption in the secondary detector system, a high energy resolution primary detector is no longer required. The primary detector system can thus be composed of densely packed layers of semiconductors designed only to provide a high degree of spatial resolution. In the back-projection equation for these emphasized events, $\Delta E$, namely the energy deposited in the primary detector by the first and only Compton scatter interaction, is not measured directly from the primary detector signal, but rather is calculated by subtracting the energy of the Compton scattered gamma ray ($E_{sc}$), as measured in the secondary detector from the known gamma-ray energy ($E_o$).

$$\Delta E = E_o - E_{sc}$$

and so also the resultant energy-loss resolution, $\sigma_{\Delta E}^{FWHM}$, is given by:

$$\sigma_{\Delta E}^{FWHM} = FWHM (E_o - E_{sc}) = FWHM (E_{sc})$$

where FWHM ($E_{sc}$) is full width at half maximum energy resolution of the secondary detector system, as measured at the scattered gamma-ray energy ($E_{sc}$).

Hence, the secondary detector system (or outer absorption layer) energy resolution becomes the limiting technological barrier. This is a much simpler technological problem to deal with because any required cooling devices that require maximal thermal contact can be directly attached to the outer surfaces, which is less difficult than cooling an inner series of layered scatter detectors that also require maximal transmission of Compton scattered gamma rays.

Furthermore, shielding of the secondary detector system from directly emitted gamma rays is not required in our design because the preferred secondary detectors of the present invention, being semiconductor based, are not as stringently limited by intrinsic "dead time" as are scintillator-based detectors of good energy resolution.

The primary detector system need only be designed to provide the spatial location of the initial Compton scatter interaction, as well as to provide a means to distinguish any gamma ray which may have Compton scattered prior to reaching the primary detector system. This requires a relatively low energy resolution detector, and accordingly may not require any cooling.

The objects and advantages of the present invention will be further appreciated in light of the following detailed description and drawings in which:

BRIEF DESCRIPTION OF THE DRAWINGS

FIG. 1 is a diagrammatic depiction of a valid event in a prior art Compton scatter camera and the associated back-projected cone surface.

FIG. 2 is a diagrammatic depiction of one section of both the primary detector system and secondary detector system that could be used in the present invention.

FIG. 3 is a schematic perspective view of a double-sided micro-strip detector that could be used as one layer in the primary detector system of FIG. 2.

FIG. 7 is a cross sectional view of a different possible Compton scatter camera, as compared with that of FIG. 6.

DETAILED DESCRIPTION

Figure 4:
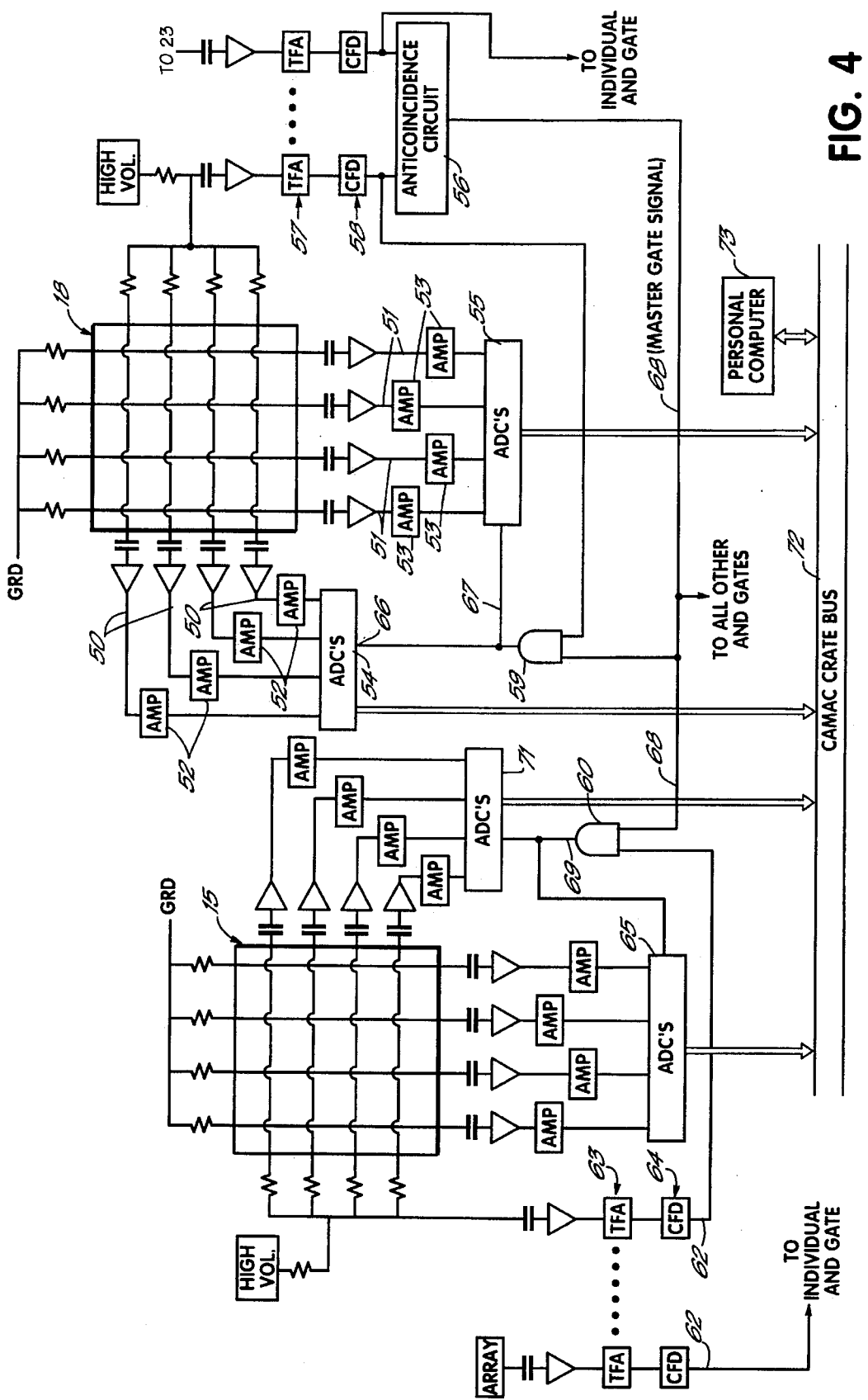
FIG. 4 is a diagrammatic depiction of the electronic circuitry that could be used for implementing the present invention.

According to the present invention, and as shown in FIG. 2, a novel Compton scatter camera consisting of one or several sections (such as in 11) is designed to image the distribution of radiation emitted from a source 12. The source is typically a radiopharmaceutical localized within a human body. The particular camera section 11 includes a primary detector system 14 and a single secondary detector 15 which is coupled with a cooling device 16.

The primary detector system 14 includes a series of individual detectors which could be silicon micro-strip detectors (18–23). In this embodiment, six separate detectors separated by spacing 26 are shown. The number of detectors and thickness of detectors are chosen to optimize the likelihood of preferred events, namely that a gamma ray emitted from source 12 will Compton scatter off of an electron within one of the primary detectors 18–23 and then be transmitted out of the primary system without further interaction in the primary system. Based on the thickness of the selected detectors, the number of detectors can be optimized.

The spacing 26 between the individual detectors 18–23 is preferably as small as possible to minimize the overall size of the section 11. Preferably, it will be less than 1 mm with a limiting factor of avoiding electronic interference between adjacent layers. This provides a closely packed array of detectors which improves resolution.

The primary detector system is then separated from the secondary detector system by an enlarged space 30 which typically will be from about 1 to about 10 cm. The larger the space, the easier it is to define the axis of the backprojected cone, but a larger spacing results in a less compact and more costly implementation.

FIG. 3 shows in more detail one of the silicon micro-strip detectors (e.g., detector 18 of FIG. 2). This detector comprises a silicon wafer 32 which includes a plurality of P-doped channels 33 on a first surface 34 and a series of N-doped channels 35 on a second surface 36. The P-channels are separated from the N-channels by an intermediate, lightly-doped portion 37. As can be seen, the channels run orthogonally to each other. Thus, when a gamma ray undergoes an interaction within the silicon wafer, the x-y coordinates within that wafer can be determined by the distribution of signals as recorded in the individual channels. The z coordinate is determined simply by noting the detector in which the Compton scatter interaction occurs.

Silicon micro-strip detectors are well known and can be purchased on the commercial market. One manufacturer of these devices is Micron Semiconductor Limited. One such device is an N-type high-resistance substrate which has 64 channels on each side. The number of PNN channels incorporated into the detectors is a matter of choice. The more channels, the more precise the x and y coordinates will be, but the more complex the electronic interface will be.

The secondary detector can be any of a variety of different detectors. However, with the Applicant's design, it is preferred to use a high energy resolution detector such as cadmium-zinc telluride (CdZnTe) or cadmium telluride (CdTe), mounted on a thermoelectric cooler or cryogenically cooled high-purity germanium. Energy resolution of 2% FWHM or better over the $E_{sc}$ energy range is likely to provide reconstructed spatial resolution at least as good as known Anger cameras. A cadmium-zinc-telluride gamma-ray detector can be purchased from AmpTek, Inc. These devices incorporate a cadmium-zinc-telluride absorptive material, in combination with a thermoelectric cooling device such as a Peltier type cooler. Cadmium-zinc-telluride detector arrays can be purchased from Aurora Technologies Corporation. Such devices can be used to provide x, y and z coordinates for the interaction, as well as measure the overall energy deposited by the interaction.

In place of Peltier-type coolers, other types of cooling devices such as standard cryogenic devices which rely on supercooled gases such as liquid carbon dioxide or liquid nitrogen can be employed to provide adequate cooling. These, of course, will be a matter of choice.

FIG. 4 shows an exemplary schematic diagram of the electronics employed in the present invention in order to illustrate the logic on which the camera is based.

In this embodiment, a primary strip-type detector 18, is shown with the individual channels connected via lines 50 and 51 through amps 52 and 53, respectively, to analog-to-digital converters 54 and 55, respectively. The composite HV (or, alternately, a resistor-coupled ground) connection will also go through an anti-coincidence circuit 56, which inputs are first directed through a timing filter amplifier 57 and a constant fraction discriminator 58 to provide a very precise timing input signal to the anti-coincidence circuit 56. If more than one input is received from the different primary detectors (e.g., 18, 19, 20, 21, 22 or 23 of FIG. 2), the anti-coincidence circuit 56 will conclude that a single gamma ray had interactions in more than one primary detector (or that more than one gamma ray interacted in the primary detector system within the resolving time) and therefore no signal will be generated from the anti-coincidence circuit 56.

If, however, only one signal is received from the plurality of primary detectors, the anti-coincidence circuit 56 will send a signal to each of the "AND" gates (e.g., 59, 60 and others not shown) which will initiate analog-to-digital (ADC) conversion and subsequent readout of each detector that has a coincident non-zero CFD signal. Note that ADCs 54, 55 may represent multiple ADCs (e.g., up to one per channel), but with a common gate signal 66, 67.

Likewise, the secondary detector system 15 includes a plurality of individual detectors (indicated by " . . . ARRAY") whose electronic interface is similar to the primary detector system 18–23, although anti-coincidence circuitry is not necessary. These detectors are side by side (as opposed to stacked) to cover the desired surrounding surface area.

If, for instance, signals are received from the anti-coincidence circuit 56 and from a CFD 58 at the same time, the "AND" gate 59 will determine that the two signals are related, i.e., caused by the same gamma ray, and will generate a master gate signal for ADC gates 66 and 67 to cause the signals from the analog-to-digital converter arrays 54, 55 to be directed to the (CAMAC crate) bus 72. This will input the information into the computer 73, which will store all of the energy signals gated from the primary and secondary detectors, as well as the x, y and z coordinates of the measured interactions. "AND" gates (59, 60 and others not shown) will be used to restrict ADC readout to only that primary and those secondary detectors that generate signals in coincidence with the anti-coincidence circuit 56, thus markedly reducing read-out dead time and memory consumption. If energy is deposited in the secondary detector system 15 but the anti-coincidence circuit 56 does not produce a simultaneous output, this may indicate that there was no interaction in the primary detector system and accordingly that information would not be gated to the computer for this logic.

The stored data for each event, i.e., sequence of a single Compton scatter in the primary system followed by absorption in the secondary system, is used to compute the location from which the gamma ray was emitted for use in generating an output image. Software analysis can also be used to eliminate some "bad" events due to "impossible" kinematic sequences, or other. The data can be further manipulated so that the energies obtained from a single gamma ray at the primary and secondary detectors are combined together and compared to the $E_o$ which will be known—for example, 140 keV for $^{99m}$Tc. If the combined energies are significantly less than $E_o$, that data can be disregarded because it indicates that the gamma ray had a Compton scatter interaction prior to its interaction in the primary detector system.

Further, if the sum value of the interaction energies was significantly different from $E_o$, this could be disregarded as an erroneous event. The "software" energy discrimination levels can be approximately $E_o \pm \frac{2}{3}$ FWHM of the primary detector system.

The logic of the present invention provides three features. First, the anti-coincidence circuitry will ignore any gamma ray that has more than one collision in the primary detector system 18. Secondly, the primary detector 18 is not used to compute $\Delta E$. Rather, its energy signal, when added to that of the coincident secondary, is only used to provide a rough estimation of the total deposited energy in order to compare this to the actual known value of $E_o$ (140 keV for technetium-99m) to determine whether or not the gamma ray was Compton scattered prior to reaching the primary detector 18, and then ignoring the event if it had such a prior interaction. Finally, $\Delta E$ is determined by measuring the energy deposited in the secondary detector system ($E_{sc}$) and simply subtracting this from the known $E_o$ value. Hence, the secondary detector system (or outer absorption layer) energy resolution becomes the limiting technological barrier.

The Compton camera shown in FIGS. 2 and 4 is exemplary and can be modified. For example, pixel-based detectors and/or drift type detectors might be used instead of micro-strip based detectors. Pixel based detectors would enhance the energy resolution characteristics, but would severely add to the complexity of electronics (e.g., instead of 64+64 strips per board, there would be 64×64 total pixels per board for the same spatial resolution). Drift type detectors offer electronic simplicity, however they are generally intrinsically slow and so would not work well without some shielding.

Charge division readout could be employed in the microstrip signal processing circuitry (requiring, usually, 4 ADC's per detector, 2 for each side, rather than the one ADC per channel as is presently shown in FIG. 4). Such charge division circuits have been used successfully, but require detailed calibration because the energy signals would have some position dependence. However, of all readout circuit modifications, this one might be the most desirable.

A major electronic simplification of the FIG. 4 circuit is to only read out the channel "bit pattern" of the primary detector system together with one or two total energy signals from each micro-strip detector. This could be accomplished by replacing the Amps 52 and 53 with single channel analyzers (SCAs) and replacing the ADC arrays 54 and 55 with bit pattern latch/readout circuits. Additionally, for recording the energy signal, an AMP and ADC would be tied in parallel with the TFA and CFD circuits 57 and 58, with a second AMP and ADC added to the GRD side (with resistor buffering). Both of these ADCs would use the same master gate signals, 66 and 67, as were used previously. Even though the electronics would be far less costly and greatly simplified, the disadvantages of this implementation would be a degradation of energy resolution in the primary system signal (for discriminating against source scatter) and also the reduction of the ability to software-analyze the events (e.g., against chance coincidences in same board). If the energy resolution with this methodology proves to be adequate, these same simplifications could be made to the secondary detector system.

A minor electronic simplification would be to add a second anti-coincidence circuit (or possibly a multi-input "OR" gate) having inputs 62. The output of this circuit would then be used as an input to an "AND" gate together with the output of anti-coincidence circuit 56, and the output of this "AND" gate would then become the master gate signal. This modification would eliminate events which had one interaction in the primary system followed by no further interactions in the secondary system.

The following equations and numerical examples will illustrate the importance of good "dE" resolution, as well as the importance of having the first Compton scatter interactions occur as closely as possible to the source of gamma-ray emissions, for obtaining good reconstructed spatial resolution ($\Delta S$). Consider an incident gamma ray of energy $E_o$ scattering at angle $\theta$ off of a free electron. If the detector spatial resolution is not considered to be a limiting factor, then the following functional relationship exists between the FWHM uncertainty in the back-projected cone half-angle ($\sigma_\theta^{FWHM}$) and the FWHM uncertainty in the energy deposited in the primary detector ($\sigma_{\Delta E}^{FWHM}$).

$$\sigma_\theta^{FWHM}(\text{radians}) = \frac{[1 + \alpha(1 - \cos\theta)]^2}{\alpha \sin\theta} \times \frac{\sigma_{\Delta E}^{FWHM}}{E_0}$$

Figure 5:
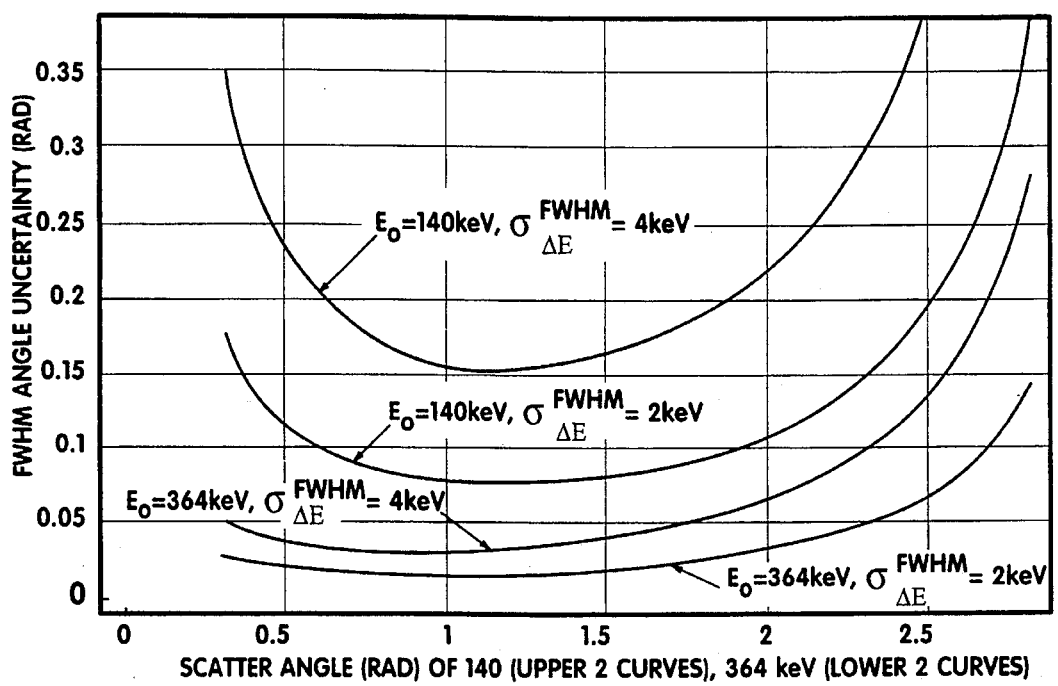
FIG. 5 is a graph showing the FWHM angle uncertainty, for 0 to $\pi$ radians scattering angle and 140 keV and 364 keV incident energies.

FIG. 1 shows the backprojection cone and the associated uncertainty in the cone half angle $\sigma_\theta^{FWHM}$. FIG. 5 shows this half-angle uncertainty for 140 and 364 keV emitted gamma-ray energies from 0 to $\pi$ radians (0 to 180 degrees) scatter angle, and for two values of $\sigma_{\Delta E}^{FWHM}$. This half-angle uncertainty directly relates to the resulting positional uncertainty by only a factor of the distance to the reconstruction point from the cone apex: $\Delta S = d \times \sigma_\theta^{FWHM}$, where d is the distance of the source from the Compton scatter interaction. In actual fact, for a particular point-source location of emitted gamma rays, $\Delta S$ would be approximately the average value of all such backprojected cone calculations. Note also from FIG. 5 that the system spatial resolution will improve with increasing emitted gamma-ray energy. This trend is just opposite to that observed with current Anger camera technology which suffers from septal penetration in the collimator at higher energy gamma rays resulting in a more blurred image with increasing energy.

As a typical numerical example in the use of these graphs, consider a 140 keV emission, from a source 10 cm distant from the scatter layers, scattering at angle 1.5 radians (=86°). The resultant energy $E_{sc}$ will be approximately 112 keV. Published data from Amp Tek, Inc. (Huber, Pantazis, Jordanov (Amptek)—*High Performance, Thermoelectrically Cooled X-Ray and Gamma Ray Detectors*, INT'L CONFERENCE ON THE APPLICATION OF ACCELERATORS IN RESEARCH AND INDUSTRY (Invited Paper), Denton, Texas, November 1994, pp. 1–4) show that CdTe diodes mounted to their Peltier cooling devices display: 1.27 keV FWHM at 59.4 keV, 1.7 keV FWHM at 122 keV, and 13.0 keV FWHM at 662 keV. *Pantazis*, et al. has published some measurements using CdZnTe and with that it is seen: (FWHM CdZnTe)/(FWHM CdTe) at 122 keV~1.7/1.3. With these values, one can interpolate and adjust to find the resolution values needed. At 112 keV this is~1.5×(1.7/1.3)= 2.0 keV FWHM in Peltier Cooled CdZnTe. Taking this value to FIG. 5 and reading from the 2.0 keV plot (2nd from top) at 1.5 radians, $\sigma_\theta^{FWHM}=0.08$ radians. Which when multiplied by d=10 cm yields $\Delta S=0.8$ cm FWHM. The best state-of-the-art resolution values in the reconstructed image for Anger cameras are $\Delta S \sim 0.7$ cm FWHM at d=5 cm, and $\Delta S \sim 1.0$ cm at d=10.0 cm and for 140 keV gamma rays. And the results for the Applicant's system improve further with increasing energy (while those for an Anger camera get worse). With 364 keV emission energy, the final value for this same calculation is $\Delta S=0.55$ cm FWHM. And halving the distance (e.g., brain imaging) will even halve these resolution values. (Note that these resolution calculations would even improve further by using the more expensive HPGe).

In this design, the scatter layers can be in close proximity with each other because only an anti-coincidence signal is required between them. In contrast, a significant spacing is necessary if successive multiple scatter interactions are required for reconstruction. Hence, instead of the 1 cm spacing of 20 layers, as proposed by Kamae, et al. and Dogan, et al., the presently proposed system could probably tolerate about 1 mm spacing between the scatter layers (or even a densely packed, zero-spacing array). This would allow for a much more compact arrangement when the final working clinical system is extended to a fully source-surrounding geometry. As discussed above in the equation for $\Delta S = d \times \sigma_\theta^{FWHM}$, closer proximity of the initial scatter interaction to the source location will proportionally improve reconstruction spatial resolution.

Figure 6:
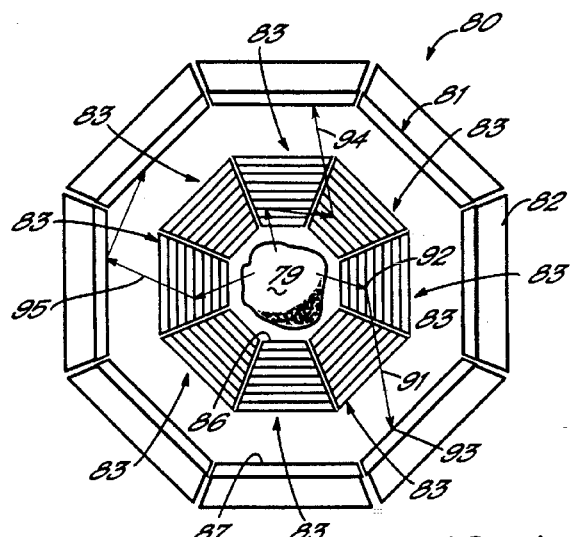
FIG. 6 is a cross-sectional view of a possible three-dimensional Compton scatter camera formed according to the method of the present invention.

FIG. 6 shows a preferred embodiment of the present invention, 360° Compton scatter camera 80 adapted to measure gamma rays from source 79. In this embodiment, the entire periphery is a mutually disconnected series of cadmium-zinc-telluride secondary detectors 81, each cooled with a series of Peltier coolers 82. Interior to this are a plurality of segmented primary detectors 83 that completely surround source 80. The primary detectors 83 are layered silicon micro-strip detectors, as previously described.

In this embodiment, the distance from the edge 86 of the primary detector 83 to the edge 87 of the secondary detector can be from~2–12 cm (e.g., primary-to-secondary in the same section).

As with the Compton scatter camera section shown in FIG. 2, a gamma ray emitted from source 79 (in FIG. 6) interacts in detectors 81 and 83.

Line 91 depicts the interaction sequence of a typical preferred event. The gamma ray comes from the source 79 and passes through four primary detector layers 83 and a Compton scatter interaction occurs at 92. The gamma ray then passes through the remaining primary detector layers and is absorbed in secondary detector 81 at point 93. This is a preferred (emphasized) event because it had only one Compton scatter in the primary detector and then was absorbed in the secondary detector system.

Line 94 shows the path of a gamma ray having a less preferred interaction sequence. The gamma ray represented by line 94 has two collisions in the primary detector 83. Therefore, the information obtained from this event would not be stored or further analyzed if the logic of FIG. 4 were employed. The anti-coincidence circuit 56 would filter this out. The gamma ray path represented by line 95 has two collisions in the secondary detector 81. This might be processed as a good event by summing the two secondary interactions as $E_{sc}$, and discerning, through kinematics, which occurred first.

It is interesting to note that for a 1.0 cm thickness of silicon—for example, 10 layers of 1 mm each—the probability of a single Compton scatter interaction followed by subsequent escape of the scattered gamma ray without undergoing further interaction in the layers is over 15% of events when the detection threshold is 1.5 keV. This reduces to about 10% of all events when the worst-case scenario threshold of 10 keV is employed. This is typically at least a 100-fold improvement over Anger cameras that typically image one gamma ray per 1500 emitted. In a triple-headed Anger camera, that is one in 4,500 per head. However, with the eight-section segmented Compton scatter camera shown in FIG. 6, the number of detected gamma rays would be approximately $8^2$ or 64 times more sensitive than would a single section (or segment) equivalent because the secondary detector segment may receive the scattered gamma rays of any primary detector segment.

Further, it must be noted that even though we have indicated that "single scatter only in the primary system followed by absorption in the secondary system" events are preferred as the major source of reconstruction information, other events might also be included with slight modifications to the electronics of FIG. 4. In fact, any event which includes a first Compton scatter interaction (in the primary system or secondary system) followed directly or indirectly (through multiple Compton) by full $E_{sc}$ energy absorption (in the primary system or secondary system), is a candidate for inclusion in the reconstruction process. Hence, event interaction sequences denoted by lines 94 and 95 of FIG. 6 would be good events in this scenario. Such events would probably not have the same quality of backprojected resolution as those events depicted in FIG. 1, and so their inclusion in the reconstruction would possibly be with different "weighting". In fact, with iterative reconstruction techniques such as "maximum likelihood", any additional variables which are correlated with radioisotope distribution can be included in the reconstruction data.

With these points in mind consider the following minor modifications to the circuit of FIG. 4 that would allow for the acquisition and inclusion of these other interaction sequence events:

a) A logic gate having inputs 62 which would open if and only if two or more inputs were registered simultaneously. The output of this circuit would then be input to an "OR" gate together with the output of anti-coincidence circuit 56, and then the output of this OR gate would become the master gate signal. This modification would allow for direct secondary-to-secondary interaction event sequences, which had no interaction in the primary system, to be gated and included.

b) Replacement of anti-coincidence circuit 56 by a multiple input "OR" gate (opens if one or more inputs are non-zero). This would allow for the inclusion of events which undergo primary-to-primary interaction sequences (e.g., multiple scattering, or scatter then absorption in the primary system). Note further that if the primary system were comprised of HPGe detectors, then this modification would be highly desirable, and in fact the whole secondary system might possibly be eliminated.

c) A combination of a) and b) above, allowing for inclusion of both of these additional interaction sequences. This combined modification would allow for acquisition and inclusion of all events which had a first Compton interaction followed directly or indirectly by absorption in any sequence of primary or secondary system detectors.

FIG. 7 shows a simpler embodiment of the present invention. In this embodiment, there is a Compton scatter camera 101 with primary detector system 102 and one secondary detector system 103. The secondary detector system 103 comprises a back detector panel 104 and associated cooling mechanism 105 such as a cryogenic cooling apparatus or a Peltier-type cooler. On the sides of primary detector system 102 are lateral detectors 106 with associated cooling devices 107. The detectors 104 and 106 are the same type secondary detectors as previously described.

The Compton scatter camera 101 can be used by itself or in conjunction with one or more identical or similar cameras to obtain a view of a source from more than one direction simultaneously.

The design of camera 101 surrounds primary detector system 102 on all sides, excepting the open primary face, with secondary detector panels. This increases the likelihood that a photon having an interaction in the primary detector system 102 will be detected by the secondary detector system.

The present invention likely provides for reduced cost, eliminates the need for collimators, provides higher spatial resolution, reduces the amount of radioactivity which must be injected into a patient, and further, reduces the time required to obtain an image. This time reduction can be very significant, not only for improved patient throughput, but also because the more time it takes to obtain an image, the more movement of the patient will occur, thus decreasing spatial resolution. Thus, the present invention is a truly significant improvement over the commonly used Anger cameras.

This has been a description of the present invention, along with the preferred method of practicing the present invention currently known to the inventors. Although described in detail with respect to gamma-ray photons, it can be used to determine spatial origin of any high-energy photon having a known energy, including X-rays and annihilation photons.

The invention itself should be defined only by the appended claims wherein we claim:

1. A method of imaging a radioactive source comprising detecting x, y and z coordinates of a Compton scatter interaction in a primary detector system by a photon emitted from said active source wherein said photon has a known energy;

measuring x, y, z coordinates and Energy ($E_{sc}$) of said photon absorbed by a secondary detector system;

determining energy deposited in said primary detector system ($\Delta E$) of said photon by subtracting $E_{sc}$ from the known energy of said emitted photon;

determining if said photon had 0, 1 or more than 1 interactions in said primary detector system;

calculating the source location of said photon if said photon had only one Compton scatter interaction in said primary detector system;

repeating these steps with additional emitted photons and summing collected source data to provide a source image.

2. The method claimed in claim 1 further comprising calculating source location of additional photons which undergo firstly a Compton Scatter interaction in any primary or secondary detector followed by subsequent total absorption and preferentially weighing data obtained from photons having had only one Compton scatter interaction in said primary detector system.

3. The method claimed in claim 2 wherein said photon is a gamma ray.

4. The method claimed in claim 1 wherein said energy deposited ($\Delta E$) is measured directly by said primary detector and added to $E_{sc}$ to determine if said photon had interacted prior to reaching said primary detector and calculating the source location of said photon only if said photon had not had such an interaction.

5. The method claimed in claim 1 wherein the source location of a photon is calculated only if said photon had only one Compton scatter in said primary detector system.

6. A Compton scatter camera comprising a primary detector system and a secondary detector system; anticoincidence means to detect if a measured photon interacts in said primary detector system more than once; means to disregard any photon interacting in said primary detector system more than once.

7. The Compton scatter camera claimed in claim 6 wherein said primary detector system comprises a plurality of segments.

8. The Compton scatter camera claimed in claim 7 wherein said primary detector system comprises a plurality of closely packed semiconductor layers.

9. The Compton scatter camera claimed in claim 8 wherein said semiconductor detectors are comprised of silicon.

10. The Compton scatter camera claimed in claim 9 wherein said secondary detector system comprises a plurality of semiconductor detectors.

11. The Compton scatter camera claimed in claim 10 wherein said semiconductor detectors are formed from a semiconductor material selected from the group consisting of cadmium-telluride, cadmium-zinc telluride, germanium, and gallium arsenide.

12. The Compton scatter camera claimed in claim 6 wherein said primary detector system is spaced from 1 to 10 cm from said secondary detector system.

13. The Compton scatter camera claimed in claim 11 wherein said secondary detector includes a cooling apparatus.

14. The Compton scatter camera claimed in claim 13 wherein said cooling apparatus comprises a Peltier-type cooler.

15. The Compton scatter camera claimed in claim 6 wherein said secondary detector system surrounds said primary detector system on all but one side of said primary detector system.

16. A method of radiodiagnostic imaging a radioactive source comprising:

detecting x, y and z coordinates of a Compton scatter interaction in a primary detector system by a photon emitted from said radiodiagnostic source wherein said photon has a known energy;

measuring x, y, z coordinates of said photon at a secondary detector system;

determining energy loss ($\Delta E$) of said photon;

determining if said photon had 0, 1 or more than 1 Compton scatter interactions in said primary detector system;

calculating the source location of said photon if said photon had only one Compton scatter interaction in said primary detector system;

repeating these steps with additional emitted photons and summing said source data to provide a source image.

17. A method of imaging a radioactive source comprising detecting x, y and z coordinates of a Compton scatter interaction in a primary detector system by a photon emitted from said active source wherein said photon has a known energy;

measuring x, y, z coordinates and Energy ($E_{sc}$) of said photon absorbed by a secondary detector system;

determining energy deposited in said primary detector system ($\Delta E$) of said photon by subtracting only $E_{sc}$ from the known energy of said emitted photon;

determining if said photon had 0, 1 or more than 1 interactions in said primary detector system;

calculating the source location of said photon if said photon had only one Compton scatter interaction in said primary detector system;

repeating these steps with additional emitted photons and summing collected source data to provide a source image.

\* \* \* \* \*